US010825171B2

(12) United States Patent
Haider et al.

(10) Patent No.: US 10,825,171 B2
(45) Date of Patent: Nov. 3, 2020

(54) METHOD AND SYSTEM FOR VISUALIZING A MEDICAL IMAGE DATA SET

(71) Applicant: Siemens Healthcare GmbH, Erlangen (DE)

(72) Inventors: Sultan Haider, Erlangen (DE); Stefan Huwer, Erlangen (DE); Mathias Nittka, Baiersdorf (DE); Zhigen Zhao, Atlanta, GA (US); Joshua Shiloh Alden, Atlanta, GA (US); Beatriz Fusaro Guimaraes, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 173 days.

(21) Appl. No.: 16/154,052

(22) Filed: Oct. 8, 2018

(65) Prior Publication Data
US 2019/0108633 A1    Apr. 11, 2019

(30) Foreign Application Priority Data
Oct. 9, 2017   (EP) .................................... 17195490

(51) Int. Cl.
*G06T 7/00* (2017.01)
*A61B 5/055* (2006.01)
(Continued)

(52) U.S. Cl.
CPC ............ *G06T 7/0012* (2013.01); *A61B 5/055* (2013.01); *G06K 9/6202* (2013.01); *G06N 20/00* (2019.01);
(Continued)

(58) Field of Classification Search
USPC ........................................................ 382/128
See application file for complete search history.

(56) References Cited

U.S. PATENT DOCUMENTS 5,410,250 A * 4/1995 Brown ................... G01R 33/56
                                                324/309
5,486,763 A * 1/1996 Alfano ................... G01R 33/56
                                                324/307
(Continued)

FOREIGN PATENT DOCUMENTS

WO       WO 9321543 A1    10/1993

OTHER PUBLICATIONS

Brunetti Arturo et al.: "White matter lesion detection in pultiple sclerosis: improved interobserver concordance with multispectral MRI display", J. Neurol, pp. 1-5, XP055460962, Retrieved from the Internet: URL:http://link.springer.com/content/pdf; 1997.
(Continued)

*Primary Examiner* — Ishrat I Sherali
(74) *Attorney, Agent, or Firm* — Schiff Hardin LLP

(57) ABSTRACT

In a method and computer for visualizing a medical image data set, in particular a magnetic resonance image data set, the medical imaging data set is provided to the computer which determines a first subset of the medical image data set related to a first parameter and a second subset of the medical image data set related to a second parameter. A first color is assigned to the first subset and a second color is assigned to the second subset. The first subset is transferred to a display in a first color presentation using the first color and the second subset is transferred in a second color presentation using the second color. The first color presentation and the second color presentation are combined for visualizing the medical imaging data set.

13 Claims, 5 Drawing Sheets

(51) Int. Cl.
*G06T 19/20* (2011.01)
*G06N 20/00* (2019.01)
*G06K 9/62* (2006.01)
*H04N 1/46* (2006.01)

(52) U.S. Cl.
CPC ............ *G06T 19/20* (2013.01); *H04N 1/465* (2013.01); *G06T 2207/10024* (2013.01); *G06T 2207/10088* (2013.01); *G06T 2219/2012* (2013.01)

(56) References Cited

U.S. PATENT DOCUMENTS

| | | | | |
|---|---|---|---|---|
| 6,956,373 | B1* | 10/2005 | Brown | G01R 33/56 324/309 |
| 8,289,329 | B2* | 10/2012 | Warntjes | A61B 5/055 345/440 |
| 8,472,684 | B1* | 6/2013 | Periaswamy | G06K 9/6289 382/128 |
| 2005/0043614 | A1 | 2/2005 | Huizenga et al. | |
| 2013/0090548 | A1* | 4/2013 | Hamilton | A61B 5/015 600/411 |

OTHER PUBLICATIONS

Search Report dated Mar. 21, 2016 for European Patent Application No. EP17195490.

\* cited by examiner

METHOD AND SYSTEM FOR VISUALIZING A MEDICAL IMAGE DATA SET

BACKGROUND OF THE INVENTION

Field of the Invention

The present invention concerns a method for visualizing a medical image data set, as well as a system and a non-transitory computer-readable data storage medium that implements such a method.

Description of the Prior Art

Visualizing medical image data sets is well known in the state of the art. For example, a medical image data set is recorded by magnetic resonance imaging and the recorded medical imaging data set is visualized by image reconstruction. As a result of such a reconstruction, a grey-scale image is presented on a display or a screen, wherein tissue types may be differentiated based on a grey scale value assigned to each pixel of the visualized medical imaging data set. However, the unambiguous identification of the tissue can be hindered due the fact that different tissues are mapped to the same grey scale value. For identifying the specific tissue, it is known to present different visualizations such as a first visualization related to a T1-relaxation time and a second visualization related to a T2-relaxation time. Thus, it is possible to present separately information that is encoded in the first visualization and in the second visualization, respectively. However, by doing so, additional information containing a structure of the data might get lost. Furthermore, a viewer has to switch his or her focus between the two visualizations. This is quite strenuous for the viewer and can lead to errors in analyzing the visualized medical imaging data sets.

Alternatively, scatter plots can be presented, such plots showing correlations between the T1-relaxation time and the T2-relaxation time inside a selected region. However, this visualization is limited to two parameters, namely the T1-relaxation time and the T2-relaxation time. Furthermore, a separation of data points with respect to their spatial locations within the image is not visually clear, when a region of interest is too large.

SUMMARY OF THE INVENTION

Based on this background, it is an object of the present invention to provide a method for visualizing a medical imaging, wherein the visualized imaging data set supports easy identification of tissue types.

According to a first aspect of the present invention a method for visualizing a medical image data set, in particular a magnetic resonance image data set, includes providing the medical imaging data set to a computer, in the computer designating a first subset of the medical image data set related to a first parameter and a second subset of the medical image data set related to a second parameter, also in the computer, assigning a first color to the first subset and a second color to the second subset, transferring the first subset to a display screen in a first color presentation using the first color and the second subset in a second color presentation using the second color, and combining, in particular merging, the first color presentation and the second color presentation for visualizing the medical imaging data set at the display screen.

In contrast to the state of the art, all information being encoded in the first subset and the second subset are presented in advance in one common visualization of the medical imaging data set. As a consequence, there is no need for the viewer to switch focus between a first visualization and a second visualization. Instead, the user is supported by the combination of the first color presentation and the second color presentation, for instance for identifying a specific type of tissue. Another advantage is that the method for visualizing is not limited to two parameters. For example at least three subsets of the medical imaging data set can be generated or provided and subsequently transferred to the respective color presentation. As a consequence, more information can be included into one common visualization. Furthermore, the method is not limited to a first color presentation and a second color presentation.

The term "combining the first color presentation and the second color presentation" preferably means that the first color presentation and the second color presentation are combined or merged pixel-by-pixel or voxel-by-voxel, i.e. a pixel of the first color visualization is combined with a corresponding pixel of the second visualization or a voxel of the first color visualization is combined with a corresponding voxel of the second visualization. For example, the pixels of the first and the second color presentations are arranged in a two dimensional array and the pixels having the same location in each array are combined. Preferably by combining the first color presentation and the second color presentation, a third color that is different from the first color and the second color is generated and visualized.

The term "color presentation" means that an intensity value of a specific color is assigned to each pixel or voxel. As a consequence, a high intensity is assigned to a tissue type and a low intensity is assigned to another tissue type. Preferably, the medical imaging data set is recorded by a magnetic resonance imaging apparatus. In general, the first parameter and the second parameter can be a T1-relaxation time, a T2-relaxation time and/or a proton density. It is also conceivable that the first parameter and/or the second parameter are related to other tissue properties that are measured with magnetic resonance (MR) methods, such as diffusion, perfusion or the like.

The present invention also encompasses a computer having a processor configured to determine a first subset of a medical image data set related to a first parameter and a second subset of the medical image data set related to a second parameter, and to assign a first color to the first subset and a second color to the second subset. The processor is further configured to transfer the first subset to a display in a first color presentation using the first color, and transfer the second subset in a second color presentation using the second color. The processor is further configured to combine, in particularly merging, the first color presentation and the second color presentation for visualizing the medical imaging data set. The computer can be incorporated into a workstation or a medical imaging apparatus or can be part of a server, part of a system of server and/or a cloud. The workstation can be a (personal) computer, a virtual running machine on host hardware, a microcontroller, or an integrated circuit. As an alternative, the workstation can be a real or a virtual group of computers. Preferably, the workstation has a calculation unit and a memory. The calculation unit can include hardware elements and software elements, for example a microprocessor or a field programmable gate array. The memory can be a non-permanent main memory (e.g. random access memory) or a permanent bulk storage (e.g. a hard disk, USB stick, SD card, solid state disk).

Preferably, the workstation is part of the medical imaging apparatus. It is also thinkable that at least one of the steps of the method is performed on a server or at the cloud.

The common visualization being result of combining the first color presentation and the second color presentation is transferred to a display or screen, such as a display of the workstation, a tablet, a smartphone or the like, and is monitored on the display of screen.

According to a preferred embodiment of the present invention, the first color presentation and the second color presentation are realized in form of layers being overlapped for combining. As a consequence, the different presentations can be combined pixel by pixel in an easy way. Furthermore, it is possible to selectively remove the first color presentation and/or the second color presentation by removing the respective layer in the visualization. Be reducing the number of layer the operator can switch, in particular individually switch, to a presentation that contains less information, when too much information is agglomerated in the common visualization.

In another preferred embodiment of the present invention, a color map is used for choosing the first color and/or the second color. In particular, it is provided that the color map is a RGB-map comprising the basic colors red, green and blue or a CMYK-map comprising the basic colors cyan, magenta, yellow and black. The first color and the second color can be mixed such that a different color result is generated by the mixing. Since RGB is the summation of light values, the colors generated by the representation are comparatively bright and the contrast is sharp. Choosing a CMYK presentation lead to a presentation, wherein grey matter shows up as green color and a tumor shows up as orange mass for example.

Preferably, for transferring the first subset into the first color presentation, a grey scale value is transferred to a color scale value of the first color for each pixel of the first subset and/or wherein for transferring the second subset into the second color presentation a grey scale value is transferred to a color scale value of the second color for each pixel of the second subset. The color scale value then represents an intensity of the color. Thus by mixing the first color presentation and the second presentation, the assigned intensities determine the color being result of mixing the first color presentation and the second color presentation. As a result, different tissues can be identified by different colors, because each tissue has a specific intrinsic value for the first parameter and/or second parameter. This allows a precise identification of the type of tissue.

The first subset and/or the second subset can be the result of correlating a subset related to a third parameter, for example the T1-relaxation time, and a subset related to a fourth parameter, for example the T2-relaxation time. That means the first subset related to the first parameter and the second sunset related to the second parameter are not directly extracted from the medical imaging data set, but are the result of a data manipulation or correlation between subsets or between visualizations being available from the medical imaging data set. Thus, it is advantageously possible to identify correlations between the subset related to the third parameter and the subset related to the fourth parameter quantitatively for supporting a further classification of tissue types. For example, the correlation of the T1-relaxation time and the T2-relaxation time can be used for identifying the tissue type. In particular, the subset related to the third parameter and the subset related to the fourth parameter are extracted from the medical imaging data set and the correlation is performed pixel per pixel. It is also possible for the first subset to be the result of a correlation and the second subset to be directly related to the T1-relaxation time, the T2-relaxation time or the like.

For assigning intensity values to the first subset and/or the second subset it is preferably provided that the method can include identifying a cluster by correlating the third parameter and the fourth parameter in a correlation level, determining a center of the identified cluster, determining a distance between each point in the cluster to the center of the identified cluster, and assigning an intensity to the pixel in the first subset and/or the second subset based on the determined distance.

Thus, it is possible to assign the result of the correlation to an intensity value that can be used for combining the first color presentation and the second color presentation. The term "cluster" preferably describes an agglomeration of similar correlation values located in the same region of the first subset and/or second subset. Furthermore, each cluster centroid/center represent a reference point. Depending on the chosen clustering model, cluster centroids or centers can be defined as the means of all data points belonging to such a cluster, or as the center of a probability density function of a distribution model, for example a Gaussian distribution for a Gaussian mixture model. For each reference point (defined by the cluster centroid) the distance between the reference point and all data point within a region of interest can then be calculated. Subsequently, the calculated distance is mapped back to the position of the corresponding pixel and thus generating the first color presentation of distance based image data.

Preferably, the distance is determined by a Euclidean distance, by a Mahalanobis distance, a cosine similarity and Manhattan distance and/or the like. The advantage of using a Euclidean distance is providing a stable performance across different quality of data sets and different clustering methods, since the calculation of Euclidean distance does not require any additional information such as a covariance matrix. The advantage of using a Mahalanobis distance is taking into account the shape and size of the cluster and therefore sharper images can be produced compared to a visualization being result of calculating the Euclidean distance. Preferably, the covariance matrix is taken into account.

In another embodiment of the present information, a principal component analysis is used for reducing the number of parameters. Thus, it is possible to reduce the number of color presentation to the maximal number of basic color being available in the selected color map (maximal number of color channels in the RGB representation: 3; maximal number of color channels in the CMYK representation: 4). As a consequence, a random number of subsets each being correlated to a parameter can be combined within a common visualization.

Preferably, a machine learning mechanism is used for identifying the cluster. For example, a deep learning mechanism can be used to train an artificial network being able to identify a cluster within a correlation between the third parameter and the fourth parameter. Advantageously the machine learning mechanism establishes a correlation between the third parameter and the fourth parameter that can be used for identifying a specific type of tissue. In particular, the artificial network is trained by analyzed medical imaging data set from the past and/or by artificial medical imaging data sets generated for training.

Furthermore, an organ and/or abnormality can be identified by correlating a third subset related to a third parameter and/or a fourth subset related the fourth parameter. It is thinkable that by comparing the correlation of the third subset and the fourth subset to previous analyzed medical imaging data sets, in particular to previous correlations, the organ and/or the abnormality recorded by the medical imaging device are automatically identified. Preferably, the user is informed by a report data set that contains the information about the organ and/or the abnormality.

In another embodiment, the first subset and the second subset are extracted from the medical imagine data set, in particular the same medical imaging data set. By extracting the first subset and the second subset from the same medical image data sets undesired shifts between the first and the second subset and consequently between the first color presentation and the second color presentation can be avoided.

In another embodiment of the invention, the medical imaging data set is recorded in a single scan. Thus, it can be avoided that the medical imaging data set for the first subset and another medical imaging data set are recorded subsequently. As a consequence, the method for visualizing is accelerated.

The present invention also encompasses a system for visualizing a medical image data set, having a computer and at least one display monitor, wherein the computer is designed, programmed or configured so as to implement any or all of the embodiments of the method according to the invention, as described above.

The present invention also encompasses a non-transitory, computer-readable data storage medium encoded with programming instructions (program code) that, when the storage medium is loaded into a computer, cause the computer to operate so as to implement any or all embodiments of the method according to the invention, as described above.

DESCRIPTION OF THE PREFERRED EMBODIMENTS

Figure 1:
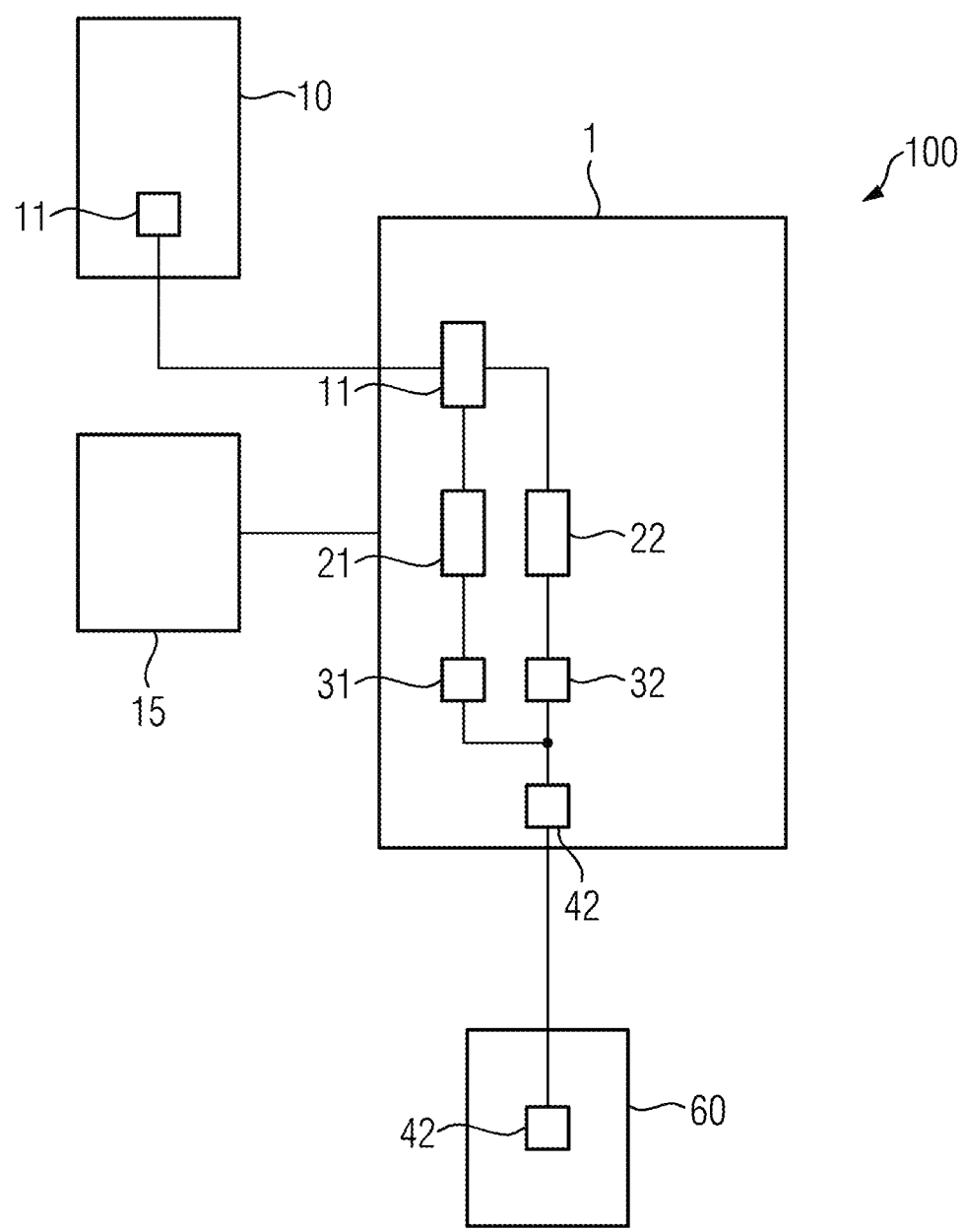
FIG. 1 schematically illustrates a system for visualizing a medical imaging data set according to a first embodiment of the present invention.

In FIG. 1 a system 100 for visualizing a medical imaging data 11 set is presented schematically. In general, the medical imaging data set 11 is provided, in particular recorded, by a medical imaging device 10, in particular a magnetic resonance imaging (MRI) device. According to the state of the art, the medical imaging data set 11 is usually presented in a grey scale image, wherein different grey levels might indicate different tissue types. However, the grey levels cannot assigned unambiguously to one specific tissue type in a common visualization. In other words: in one visualization a white region might represent a tumor or another tissue. For this reasons other visualizations of the medical imaging data set 11 are needed to verify the presence of the tumor. For example, a first subset 21 of the medical imaging data set 11 corresponding to a first parameter 51 and a second subset 22 of the medical imaging data set 11 corresponding to a second parameter 52 are visualized next to each other for comparing, for example on a screen 60 or a display according to the state of the art. Thereby, the first subset 21 preferably represents a visualization based the first parameter 51 and the second subset represented a visualization based on the second parameter 52. For the magnetic resonance imaging proceeding the first parameter 51 and/or the second parameter 52 might be a relaxation time T1, a relaxation time T2, a proton density and/or other parameters related to tissue properties, e.g. diffusion, perfusion, magnetic transfer, BOLD or the like.

Preferably, the medical imaging data set 11 is recorded in a single scan and the first subset 21 and/or the second subset 22 are extracted from the medical imaging data set 11 being result of the single scan. By recording the medical imaging data set 11 in a single scan and subsequently extracting the first subset 21 and/or the second subset 21, it is advantageously possible to provide quantitative measurements in a time efficient way. Alternatively, it is thinkable that the first subset and the second subset are recorded separately by the medical imaging device.

In order to support identifying a critical abnormality such as a tumor, the system 100 shown in FIG. 1 has a computer 1 configured for determining a first subset 21 of the medical imaging data set 11 and a second subset 22 of the medical imaging data set 11, such as by extracting the first subset 21 and the second subset 22 from a medical imaging data set 11 recorded in a single scan. Further, a first color is assigned to the first subset 21 and a second color is assigned to the second subset 22, wherein the assignment is performed automatically and/or by entering via an input device 15. Preferably, the first color and the second color are basic colors of a color model such as RGB map (three basic colors) or CMYK map (four basic colors). For example, the first color and/or the second color are red, green or blue in the case of using the RGB model.

Furthermore, the first subset 21 is transferred to a display in a first color visualization 31 and the second subset 22 is transferred in a second color visualization 32. Thereby, for transferring the first subset 21 in the first color presentation 31 a grey scale value assigned to the first subset 21 is transferred to a color scale value of the first color for each pixel of the first subset 21, and/or wherein for transferring the second subset 22 in the second color presentation a grey scale value assigned to the second subset 21 is transferred to a color scale value of the second color for each pixel of the second subset 21. For example for each pixel of the first subset 21 a value between 0 and 1 is assigned to labelling the grey scale. This value might be transferred to an intensity value of the first color in the first color visualization 31.

Subsequently, the first color visualization 31 and the second color visualization 32 are combined, in particular merged. As a result, the medical imaging data set 11 is visualized such that the information included in the first subset 31 and the second subset 32 are respectively presented in one common visualization 42. Preferably, the first color and the second color are mixed to a final color, in particular at each pixel. Furthermore, it is provided that the first color presentation and the second color presentation are put on top of each other for combining or merging them.

Figure 2:
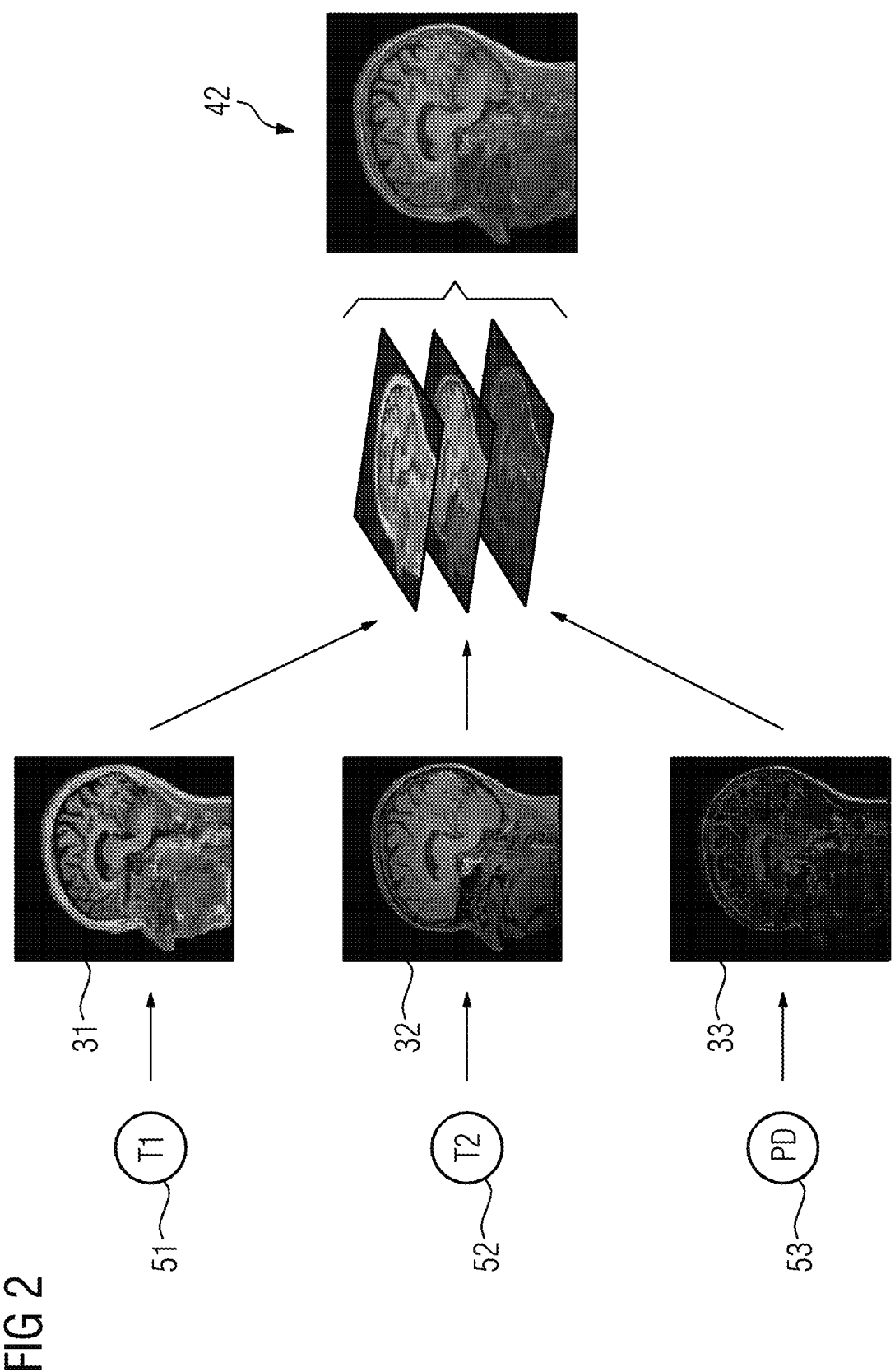
FIG. 2 is a flowchart illustrating a part of the method according to a second embodiment of the present invention.

In FIG. 2 a flowchart is shown that illustrates providing a first color presentation 31, a second color presentation 32 and a further second color presentation 33 (for a further second parameter 53) and subsequently combining the first color presentation 31, a second color presentation 32 and a further second color presentation 32 for generating a common visualization 42.

Figure 3:
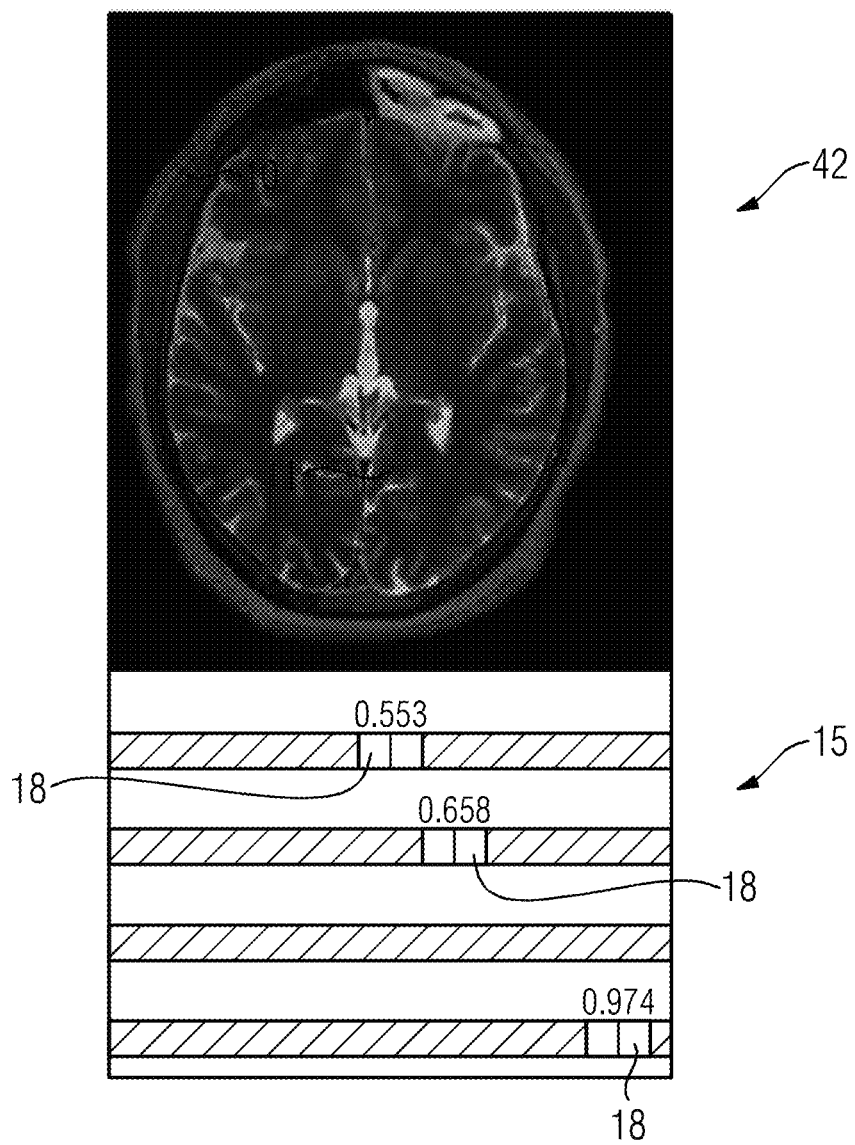
FIG. 3 shows a part of a system for visualizing a medical imaging data set according to a third embodiment of the present invention.

In FIG. 3 a part of a system 100 for visualizing a medical imaging data set 11 according to a third embodiment of the present invention is shown. In particular, according to the third embodiment, an input device 15 is provided, wherein the input device 15 is configured such that on the screen 60 a slider 18 for each parameter or color is monitored next to the common visualization 42. By shifting the respective slider 18 the influence of the first color presentation 31 or the second color presentation 32 in the common visualization 42 of the medical imaging data set 11 is weighted respectively. Thus, the input device 15 is configured for weighting influence of the first color presentation 31 or the second color presentation 32 in the visualization of the medical imaging data set 11. Preferably, this is done by adding an offset value and then wrapping the values back into a 0 to 1 range. In particular, the input device 15 comprises the slider 18 for adapting the offset value for the first color presentation 31 and a further slider 18 for adapting the offset value for the second color presentation. Thus, an operator can adjust the visualization to his preference or for highlighting a specific and individualized outcome.

Figure 4:
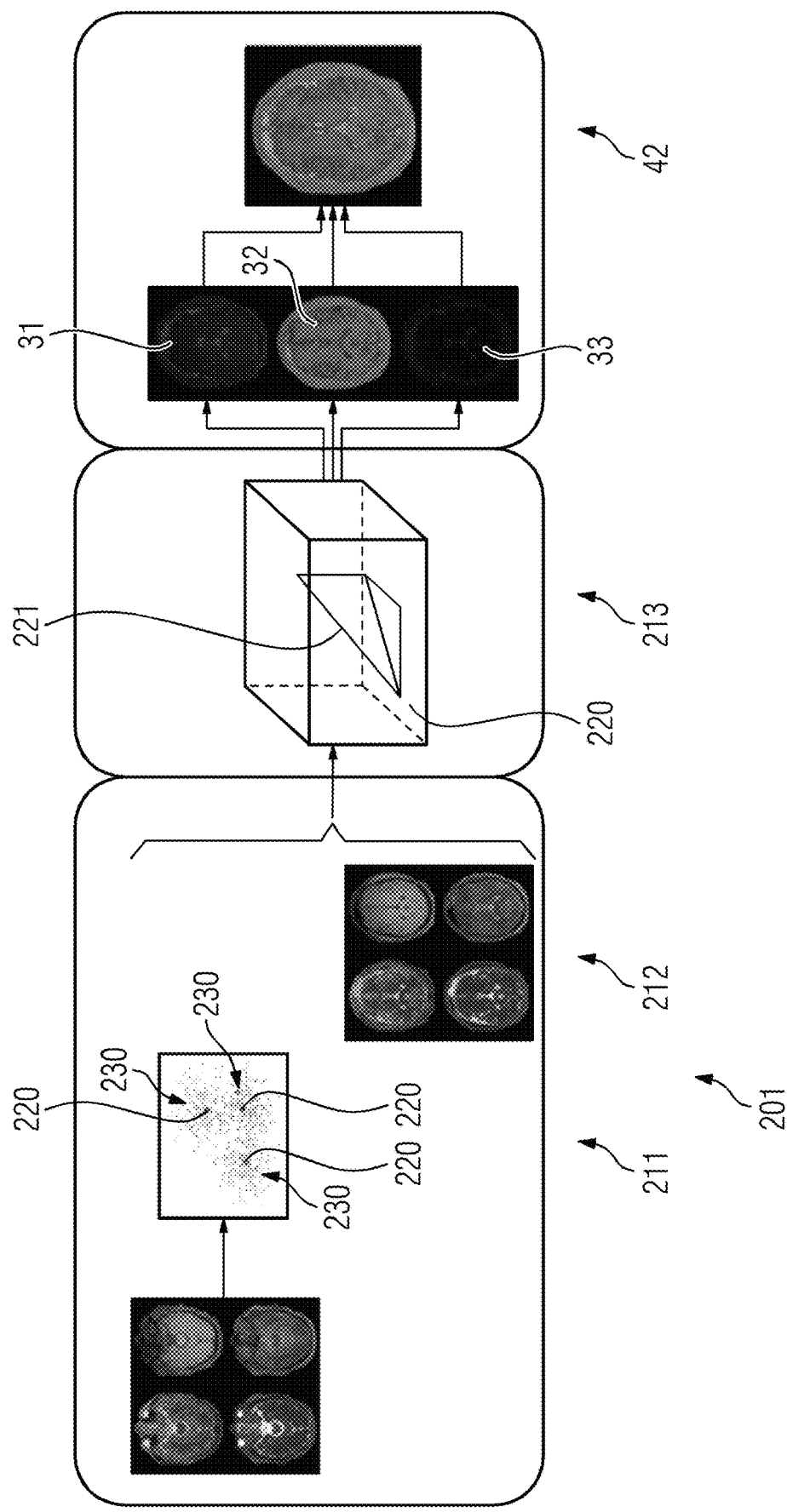
FIG. 4 is a flowchart illustrating a part of the method according to a fourth embodiment of the present invention.

In FIG. 4 a flowchart illustrating a part of the method according to a fourth embodiment of the present invention is illustrated. The method mainly corresponds to the method described in the context of the FIGS. 1 and 2 and differs only in the kind of the first parameter 51 and the second parameter 52. In particular, the first parameter 51 in FIG. 4 is represented by a correlation of a third 54 parameter, for example the T1-relaxation time, and a fourth parameter 55, for example a T2-relaxation time, and the second parameter 52 is represented by a second correlation of the third parameter 54 and the fourth parameter 55. In other words: instead of using a T1 related first subset and a T2 related second subset the result of a correlation of the T1-relaxation time and the T2 relaxation time is used as first subset. Thereby, for example the T1-relaxation time is plotted versus the T2-relaxation time for identifying 211 the correlation between the first subset 21 and the second subset 22 in a correlation level. As a result, a cluster 230, i.e. region with an increased correlation, can be identified in a correlation step. It is also thinkable that several cluster 230 are identified. These clusters 230 can be used to identify special tissue types for example. In order to incorporate the information being encoded in the correlation, in step 212 a center 220 of each cluster is determined in step 213 and a distance 221 to the center 230 is determined for each point in the cluster 230 in the correlation level. As a consequence, an intensity value is assigned to each determined distance 221, in particular in the first color presentation 31 and/or the second color presentation 32 of the medical image data set 11. Subsequently, the first color presentation 51 and the second color presentation 52 originating from the correlation of the T1-relaxation time and the T2-relaxation time are combined to the common visualization 42 of the medical imaging data set 11.

Figure 5:
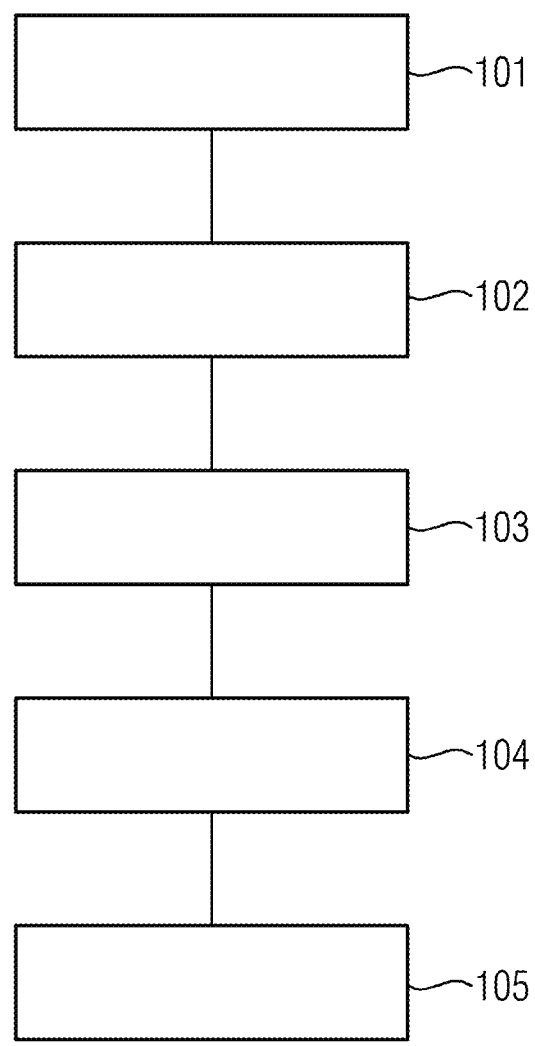
FIG. 5 is a flowchart illustrating a method according to a fifth embodiment of the present invention.

In FIG. 5 a flowchart of a method according the present invention is illustrated, wherein the method includes step 101 in which the medical imaging data set 11 is provided to the computer 1, and extracting in step 102, a first subset 21 of the medical image data set 11 related to a first parameter 51 and a second subset 22 of the medical image data set 11 related to a second parameter 52. In step 103 a first color is assigned to the first subset 21 and a second color to the second subset 22. In step 104, the first subset 21 is transferred to a display in a first color presentation 31 using the first color and the second subset 32 is transferred in a second color presentation 32 using the second color. In step 105, the first color presentation 31 and the second color presentation 32 are combined preferably by merging, for visualizing the medical imaging data set 11.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for visualizing a medical image data set, comprising:
    providing a medical imaging data set to a computer;
    in said computer, extracting a first subset, related to a first parameter, from said medical image data set by correlating pixels of said first subset with pixels of a subset related to a third parameter, and extracting a second subset, related to a second parameter, from said medical image data set by correlating said pixels of said second subset with pixels of subset related to a fourth parameter, wherein each of said first subset and said second subset is comprised of pixels;
    identifying at least one of an organ or an anatomical abnormality said correlation with said third parameter and said correlation with said fourth parameter;
    in said computer, assigning a first color to said first subset and assigning a second color to said second subset;
    transferring the first subset from said computer to a display screen in a first color presentation using said first color, and transferring said second subset from said computer to said display screen in a second color presentation using said second color; and
    at said display screen, combining said first color presentation with said second color presentation in order to visualize said medical imaging dataset at said display screen with a color that is a combination of said first color and said second color.

2. The method as claimed in claim 1 comprising combining said first color presentation and said second color presentation by merging said first color presentation with said second color presentation at said display screen.

3. The method as claimed in claim 1 comprising combining said first color presentation and said second color presentation by overlapping said first and second color presentations with each other at said display screen.

4. The method as claimed in claim 1 comprising, in said computer, using a color map to select at least one of said first color and said second color.

5. The method as claimed in claim 1 wherein transferring said first subset in said first color presentation comprises transferring a grey scale value to a color scale of said first color for each pixel of said first subset, and wherein transferring said second subset in said second color presentation comprises transferring said grey scale value to a color scale of said second color for each pixel of said second subset.

6. The method as claimed in claim 1, comprising:
    assigning intensity values to said pixels of said first subset by identifying a first cluster of pixels of said first subset by said correlation with said pixels of said subset related to said third parameter, determining a center of said first cluster, determining a distance between each pixel in said first cluster and said center of said first cluster, and assigning an intensity value to each pixel in said first cluster dependent on said distance; and assigning intensity values to said pixels of said second subset by identifying a first cluster of pixels of said second subset by said correlation with said pixels of said subset related to said fourth parameter, determining a center of said first cluster, determining a distance between each pixel in said first cluster and said center of said first cluster, and assigning an intensity value to each pixel in said first cluster dependent on said distance.

7. The method as claimed in claim 6 comprising executing a principal component analysis in said computer to reduce a number of said parameters.

8. The method as claimed in claim 6 comprising executing a machine learning algorithm in said computer in order to identify said first cluster and said second cluster.

9. The method as claimed in claim 1 comprising providing said medical image data set to said computer as a medical image data set recorded in a single scan.

10. The method as claimed in claim 1 comprising providing a first input to said computer that gives said first color presentation a first color weighting, and providing a second input to said computer that gives said second color presentation a second color weighting, and combining said first and second color presentations with said first color weighting and said second color weighting in order to produce said combined color in said visualization of said medical image data set.

11. A medical imaging apparatus comprising:
a medical image data acquisition scanner operable to obtain a medical imaging data set;
providing said medical imaging data set to a computer;
said computer being configured to extract a first subset, related to a first parameter, from said medical image data set by correlating pixels of said first subset with pixels of a subset related to a third parameter, and extract a second subset, related to a second parameter, from said medical image data set by correlating said pixels of said second subset with pixels of subset related to a fourth parameter, wherein each of said first subset and said second subset is comprised of pixels;
said computer being configured to assign intensity values to said pixels of said first subset by identifying a first cluster of pixels of said first subset by said correlation with said pixels of said subset related to said third parameter, determining a center of said first cluster, determining a distance between each pixel in said first cluster and said center of said first cluster, and assigning an intensity value to each pixel in said first cluster dependent on said distance;
said computer being configured to assign intensity values to said pixels of said second subset by identifying a first cluster of pixels of said second subset by said correlation with said pixels of said subset related to said fourth parameter, determining a center of said first cluster, determining a distance between each pixel in said first cluster and said center of said first cluster, and assigning an intensity value to each pixel in said first cluster dependent on said distance;
said computer being configured to assign a first color to said first subset and to assign a second color to said second subset;
said computer being configured to transfer the first subset from said computer to a display screen in a first color presentation using said first color, and to transfer said second subset from said computer to said display screen in a second color presentation using said second color; and
said computer being configured to combine, at said display screen, said first color presentation with said second color presentation in order to visualize said medical imaging dataset at said display screen with a color that is a combination of said first color and said second color.

12. The medical imaging apparatus as claimed in claim 11 wherein said medical image data acquisition scanner is a magnetic resonance scanner.

13. A non-transitory, computer-readable data storage medium encoded with programming instructions, said storage medium being loaded into a computer and said programming instructions causing said computer to:
receive a medical imaging data set to a computer;
extract a first subset, related to a first parameter, from said medical image data set by correlating pixels of said first subset with pixels of a subset related to a third parameter, and extract a second subset, related to a second parameter, from said medical image data set by correlating said pixels of said second subset with pixels of subset related to a fourth parameter, wherein each of said first subset and said second subset is comprised of pixels;
identify at least one of an organ or an anatomical abnormality by said correlation with said third parameter and said correlation with said fourth parameter;
assign a first color to said first subset and assign a second color to said second subset;
transfer the first subset from said computer to a display screen in a first color presentation using said first color, and transfer said second subset from said computer to said display screen in a second color presentation using said second color; and
at said display screen, combine said first color presentation with said second color presentation in order to visualize said medical imaging dataset at said display screen with a color that is a combination of said first color and said second color.

* * * * *